(12) United States Patent
Reiner

(10) Patent No.: US 7,849,115 B2
(45) Date of Patent: Dec. 7, 2010

(54) METHOD AND APPARATUS FOR ADAPTING COMPUTER-BASED SYSTEMS TO END-USER PROFILES

(76) Inventor: Bruce Reiner, 6 Greenleaf La., Seaford, DE (US) 19973

( * ) Notice: Subject to any disclaimer, the term of this patent is extended or adjusted under 35 U.S.C. 154(b) by 377 days.

(21) Appl. No.: 11/806,924

(22) Filed: Jun. 5, 2007

(65) Prior Publication Data

US 2007/0282912 A1 Dec. 6, 2007

Related U.S. Application Data

(63) Continuation-in-part of application No. 11/790,843, filed on Apr. 27, 2007, now Pat. No. 7,593,549, and a continuation-in-part of application No. 11/586,580, filed on Oct. 26, 2006.

(60) Provisional application No. 60/810,655, filed on Jun. 5, 2006.

(51) Int. Cl.
*G06F 17/00* (2006.01)
(52) U.S. Cl. ............... 707/912; 707/200; 707/104.1
(58) Field of Classification Search ............... 707/912, 707/999.2, 104.1
See application file for complete search history.

(56) References Cited

U.S. PATENT DOCUMENTS

| | | | |
|---|---|---|---|
| 5,867,812 A | 2/1999 | Sassano | |
| 5,876,926 A | 3/1999 | Beecham | |
| 5,912,818 A | 6/1999 | McGrady et al. | |
| 5,924,074 A | 7/1999 | Evans | |
| 5,930,804 A | 7/1999 | Yu et al. | |
| 6,031,910 A | 2/2000 | Deindl et al. | |
| 6,044,349 A | 3/2000 | Tolopka et al. | |
| 6,070,141 A | 5/2000 | Houvener et al. | |
| 6,081,750 A | 6/2000 | Hoffberg et al. | |
| 6,390,979 B1 * | 5/2002 | Njemanze | 600/438 |
| 6,532,459 B1 * | 3/2003 | Berson | 707/3 |
| 6,613,000 B1 * | 9/2003 | Reinkensmeyer et al. | 600/587 |
| 7,181,438 B1 * | 2/2007 | Szabo | 707/2 |
| 7,299,217 B2 * | 11/2007 | Oni | 707/1 |
| 7,366,709 B2 * | 4/2008 | Nevin et al. | 707/1 |
| 7,401,098 B2 * | 7/2008 | Baker | 707/104.1 |
| 2002/0010679 A1 | 1/2002 | Felsher | |
| 2002/0132214 A1 * | 9/2002 | Mattson et al. | 434/323 |
| 2003/0088441 A1 | 5/2003 | McNerney | |
| 2003/0204481 A1 | 10/2003 | Lau | |
| 2004/0054923 A1 | 3/2004 | Seago et al. | |
| 2004/0117215 A1 | 6/2004 | Marchosky | |
| 2004/0122709 A1 | 6/2004 | Avinash et al. | |
| 2005/0101841 A9 | 5/2005 | Kaylor et al. | |

(Continued)

*Primary Examiner*—Don Wong
*Assistant Examiner*—Shyue Jiunn Hwa
(74) *Attorney, Agent, or Firm*—Jean C. Edwards, Esq.; Akerman Senterfitt

(57) ABSTRACT

The present invention relates to a method of adapting computer programs to user profiles, including providing a user with a questionnaire to determine at least one of the user's intelligence, personality, emotional state, computer experience, sensory skills, motor skills, education, and training; compiling a user profile based on data received from the questionnaire; modifying the computer programs used by the user based on the user's profile; and storing the user profile and the computer program modifications in a database for future utilization by the user. The modification of the computer programs includes modifying at least one of a user interface, workstation tools, input device and navigation, image presentation, analysis of information presented, and reporting.

13 Claims, 3 Drawing Sheets

U.S. PATENT DOCUMENTS

| | | |
|---|---|---|
| 2005/0197864 A1 | 9/2005 | Koritzinsky et al. |
| 2005/0203771 A1 | 9/2005 | Achan |
| 2006/0173712 A1 | 8/2006 | Joubert |
| 2006/0229909 A1 | 10/2006 | Kaila et al. |
| 2006/0293921 A1 | 12/2006 | McCarthy et al. |
| 2007/0027715 A1 | 2/2007 | Gropper et al. |
| 2007/0055552 A1 | 3/2007 | St. Clair et al. |
| 2007/0276270 A1 * | 11/2007 | Tran .......................... 600/508 |

* cited by examiner

METHOD AND APPARATUS FOR ADAPTING COMPUTER-BASED SYSTEMS TO END-USER PROFILES

CROSS-REFERENCE TO RELATED APPLICATIONS

The present application claims priority from U.S. Provisional Patent Application No. 60/810,655, filed Jun. 5, 2006, and is a continuation-in-part (CIP) of U.S. patent application Ser. Nos. 11/790,843, filed Apr. 27, 2007 now U.S. Pat. No. 7,593,549, and Ser. No. 11/586,580 filed Oct. 26, 2006, the contents of both applications which are herein incorporated by reference in their entirety.

BACKGROUND OF THE INVENTION

1. Field of the Invention

The present invention relates to a method and apparatus for adapting computer-based technologies to each end-user. More specifically, the present invention relates to a dynamic profiling system that takes into account the multiple variables that uniquely distinguish the population of end-users, in addition to the temporal changes that occur within each end-user over time.

2. Description of the Related Art

In its present form, existing technology development is a "one size fits all" approach, with limited ability to adjust functionality to the end-user's unique needs and preferences. Regardless of whether the product is an automobile global positioning system (GPS), medical information system (i.e., electronic medical record (EMR)), bank automated teller machine (ATM), or personal computer software program (i.e, Microsoft PowerPoint), the same limitations in end-user customization holds true.

One of the major disadvantages of existing engineering protocols is that the software developers receive little if any feedback after the product is developed and goes into everyday use. Feedback often takes the form of a limited number of advisory group members, who are not truly representative of the community at large, both in clinical practice and personality. If technology is to be truly adaptive, it must be continually monitored and updated, based on the specific needs and patterns of us by its community of end-users.

Computer-based technologies are largely inflexible and created in the eyes of the engineering team that design them. While periodic upgrades will address some of the perceived technical flaws, these technologies are largely developed to address the needs of large groups of users, as opposed to individual users. If an individual end-user is to get the most efficient use of the technology and specific product being used, his/her individual strengths and weaknesses, biases, and perceptions must be taken into account. At the same time, each end-user is not a fixed or static entity. During the course of time, an individual end-user dynamically changes in a variety of ways including (but not limited to) education and training, experience, stress, fatigue, and adaptability.

Accordingly, a way of adapting computer-based technologies to end-user profiles, which could make access, usage, and training, easier and more efficient for users, and adapt for each user's changes over time, is desired.

SUMMARY OF THE INVENTION

The present invention relates to a method and apparatus for adapting computer-based technologies to each end-user. More specifically, the present invention relates to a dynamic profiling system that takes into account the multiple variables that uniquely distinguish the population of end-users, in addition to the temporal changes that occur within each end-user over time. The present profiling system would be supported by an automated data collection tool that would continuously update each individual and collective users workflow and use of computer tools and programs, thereby providing objective feedback as to how computer functionality changes within different sub-groups of users. The combined data (from end-user profiling and computer-based auditing) may be used to collectively provide feedback to technology product developers to utilize end-user driven upgrades and product refinements. In the end, the paradigm of technology product development is changed from an "engineering-driven" to an "end-user driven" process.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to a dynamic profiling system that takes into account the multiple variables that uniquely distinguish the population of end-users, in addition to the temporal changes that occur within each end-user over time. The present profiling system may be supported by an automated data collection tool that would continuously update each individual and collective users workflow and use of computer tools and programs, thereby providing objective feedback as to how computer functionality changes within different sub-groups of users. The combined data (from end-user profiling and computer-based auditing) may be used to collectively provide feedback to technology product developers to utilize end-user driven upgrades and product refinements.

Figure 1:
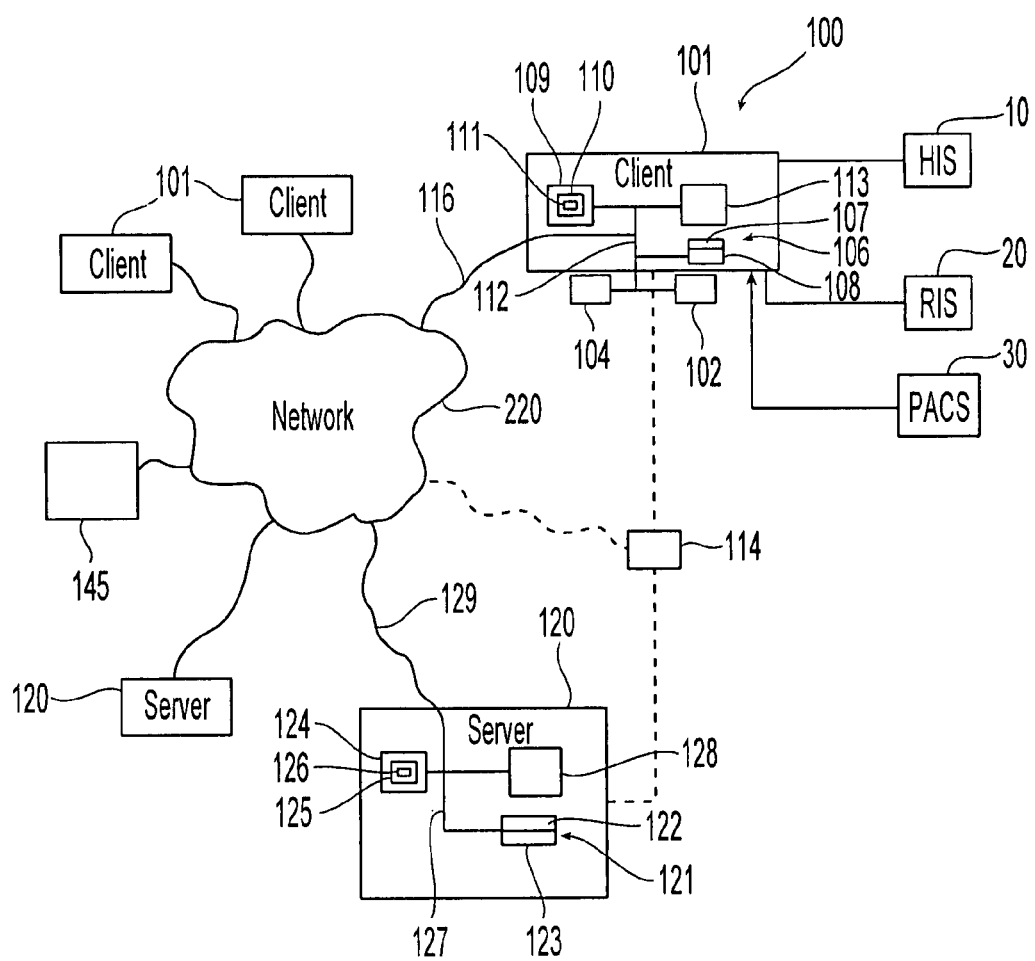
FIG. 1 shows a schematic diagram of one embodiment of the dynamic profiling system according to one embodiment consistent with the present invention.

The dynamic profiling system 100 of the present invention (see FIG. 1) includes a client computer 101, such as a PC, and includes a display device 102 capable of providing high resolution of images. However, the client 101 may be a mobile terminal, such as a mobile computing device, a cellular telephone, or a mobile data organizer (PDA), operated by the user accessing the system 100 remotely from the client 101.

An input means 104 or user selection means, including hot clickable icons etc., or selection buttons, in a menu, dialog box, or a roll-down window of an interface, are provided at the client 101, and the user may input commands through a programmable stylus, keyboard, mouse, speech processing means, laser pointer, touch screen, or other input means 104.

The input or selection means 104 may be constituted by a dedicated piece of hardware or its functions may be executed by code instructions executed on the client processor 106, involving the display unit 102 for displaying the selection window and a stylus or keyboard for entering a selection, for example.

The input means 104 is configured to accept the input from a biometric input means 35. The biometric input means 35 includes equipment such as a fingerprint scanner, a palm scanner, a microphone for voice recognition, a camera for face or retina recognition and photo identification, wrist scanner for venous flow identification, an electronic signature pad for electronic signature verification, etc., which is integrated with the client computer 101, and/or with imaging or other equipment. The biometrics technology may be currently available or future-conceived. The biometrics input means 35 may be provided separately or integrated with the client 101.

The client 101 typically includes a processor 106 as a client data processing means, the processor including a central processing unit (CPU) 107 or parallel processor and an input/output (I/O) interface 108, a memory 109 with a program 110 having a data structure 111, all connected by a bus 112. Further, the client 101 may include one or more secondary storage devices 113. The bus 112 may be internal to the client 101 and may include an adapter to a keyboard or input device 104 or may include external connections.

The imaging display device 102 for the present invention is a high resolution touch screen computer monitor, which would allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104 which would be used to draw the gestures or symbols of the present invention, directly onto the image displaying device 102.

In addition, high resolution goggles may be used to provide end users with the ability to review images without the physical constraints of an external computer. Images could be downloaded using wireless technology and displayed on the goggles, thereby eliminating the need for a computer screen for image display. In one example, a surgeon wearing specialized high resolution goggles to display the cross-sectional radiological image of a brain tumor in 3-D format, would be able to note the gestures on the image highlighting the pathology in question and reporting pertinent characteristics (i.e., anatomic localization, size, etc.), to serve as a guide during surgery. These goggles are used for image-guided surgery, for example, and would serve to provide consultation on pertinent findings during the course of the surgery.

Note that with respect to the client system 101, the graphics user interface is a client application written to run on existing computer operating systems which may be ported to other personal computer (PC) software, personal digital assistants (PDAs), and cell phones, and any other digital device that has a screen or visual component and appropriate storage capability.

The processor 106 at the client 101 may be internal or external thereto, and executes a program 110 adapted to predetermined operations. The processor 106 has access to the memory 109 in which may be stored at least one sequence of code instructions comprising the program 110 and the data structure 111 for performing predetermined operations. The memory 109 and program 110 may be located within the client 101 or external thereto.

Note that at times the system of the present invention is described as performing a certain function. However, one of ordinary skill in the art would know that the program 110 is what is performing the function rather than the entity of the system itself.

The program 110 which runs the access system of the present invention can include a separate program code for performing a desired operation, or may be a plurality of modules performing sub-operations of an operation, or may be part of a single module of a larger program 110 providing the operation.

The processor 106 may be adapted to access and/or execute a plurality of programs 110 corresponding to a plurality of operations. An operation rendered by the program 110 may be, for example, supporting the user interface, data mining functions, performing e-mail applications, etc.

The data structure 111 may include a plurality of entries, each entry including at least a first storage area that stores the databases or libraries of biometric data, gesture symbols, or image files, for example.

The storage device 113 stores at least one data file, such as biometric data files, image files, text files, data files, audio, video files, etc., in providing a particular operation. The data storage device as storage means 113, may for example, be a database, including a distributed database connected via a network, for example. The database can be a computer searchable database and may be a relational database. The storage device may be connected to the server 120 and/or the client 101, either directly or through a communication network, such as a LAN or WAN. An internal storage device 113, or an external storage device 114 is optional, and data may also be received via a network and directly processed.

In methods and system consistent with the present invention, the client 101 may be connected to other clients 101 or servers 120, including administration, billing or other systems, via a communication link 116 as a client communication means, using a communication end port specified by an address or a port, and the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

The communication link 116 may be an adapter unit capable to execute various communications protocols in order to establish and maintain communication with the server 120, for example. The communication link 116 may be constituted by a specialized piece of hardware or may be realized by a general CPU executing corresponding program instructions. The communication link 116 may be at least partially included in the processor 106 executing corresponding program instructions.

In one embodiment consistent with the present invention, if a server 120 is used in a non-distributed environment, the server 120 would include a processor 121 having a CPU 122 or parallel processor which is a server data processing means, and an I/O interface 123, but may also be constituted by a distributed CPU 122 including a plurality of individual processors 121 on one or a plurality of machines. The processor 121 of the server 120 may be a general data processing unit, but preferably a data processing unit with large resources (i.e., high processing capabilities and a large memory for storing large amounts of data).

The server 120 also includes a memory 124 with program 125 having a data structure 126 all connected by a bus 127. The bus 127 or similar connection line can also consist external connections, if the server 120 is constituted by a distributed system. The server processor 121 may have access to a storage device 128 for storing preferably large numbers of programs for providing various operations to the users.

The data structure 126 may include a plurality of entries, each entry including at least a first storage area which stores image files, for example, but may also have alternative embodiments including that associated with other stored information as one of ordinary skill in the art would appreciate.

The server 120 may be a single unit or may be a distributed system of a plurality of servers 120 or data processing units, and may be shared by multiple users in direct or indirect connection to each other. The server 120 performs at least one server program for a desired operation, which is required in serving a request from the client 101.

The communication link 129 from the server 120 is preferably adapted to communicate with a plurality of clients.

The present invention is implemented in software which can be provided in a client and server environment, or in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

In a client-server environment, at least one client and at least one server are each connected to a network 220 such as a Local Area Network (LAN), Wide Area Network (WAN), and/or the Internet, over a communication link 116, 129. Further, even though the various systems (biometrics input means 35) are described as being directly connected to the client 101, it is known that these systems could be connected to the client over a LAN, WAN, and/or the Internet via communication links. Interaction with users may be through secure and non-secure internet connectivity. Thus, the steps in the methods consistent with the present invention are carried out at the client or at the server, or at both, the server (if used) being accessible by the client over for example, the Internet using a browser application or the like.

The client system 101 and the biometrics input means 35 may include communications via a wireless service connection. The server system 120 may include communications with network/security features, via a wireless server, which connects to, for example, voice recognition. However, one of ordinary skill in the art would know that other systems may be included.

Thus, bi-directional communication between the biometric input means 35 of the present invention, and the client 101 or additional equipment such as medical equipment, or other computers, etc., allows the input means 104 to retrieve information from the biometrics input means 35 and other systems and update information in the databases.

In another embodiment consistent with the present invention, the client system may be a basic system, and the server may include all of the components necessary to support the software platform of the present invention. Further, the present client-server system may be arranged such that the client system and/or the biometrics input means can operate independently of the server system, but that the server system can be optionally connected. In the former situation, additional modules would instead be connected to the client system. In another embodiment consistent with the present invention, the client system and server system can be disposed in one system, rather being separated into two systems.

Although the above physical architecture has been described above as client-side or server-side components, one of ordinary skill in the art would know that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations are carried out in hardware, whereas other of the above processing operations are carried out using software.

The underlying technology allows for replication to various other sites. Each new site can maintain "state" with its neighbors so that in the event of a catastrophic failure, other server systems can continue to keep the application running, and allow the system to load-balance the application geographically as required.

Further, although aspects of one implementation of the present invention are described as being stored in memory, one of ordinary skill in the art will appreciate that all or part of the methods and systems consistent with the present invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems consistent with the present invention, may contain additional or different components.

Accordingly, in one embodiment consistent with the present invention, the dynamic profiling system 100 and method includes a client computer 101 with image displaying device 102, a biometrics input means 35, and an input device 104 which is a programmable stylus, for example, connected to the computer 101 and input means 35.

Whenever an end-user logs onto a computer terminal 101—whether this means an ATM machine, a cell phone, a PDA, or any other electronic device—the end-user is requested by the program 110 to identify themselves, and to undergo authentication of their identity as described in corresponding U.S. patent application Ser. No. 11/790,843. This identification information may include a number of different identifying physical, demographic, and personality and preference characteristics. For example, the user may be requested by the program 110 to enter in biometrics information, such presenting for a photograph for facial recognition technology, submitting a fingerprint for fingerprint analysis, which is used to identify and authenticate the user. In addition, the user will be requested to enter demographic information, such as name, address, birthdate, social security number, etc., and security password to their data file, which will be used for further identification and authentication.

In one embodiment, after log-in, the user is requested to access the above identification and authentication portion of the program 110 by clicking on a hypertext link provided on the display 102. Further, any identification and authentication data, including the biometrics data inputted into the system 100, and the demographic information inputted at the client 101, is preferably stored at a server 120 or in a data storage 113, 128 etc. accessed over the internet 220. memory or a database 109, 113, 128, etc., such that pertinent information can be retrieved, sorted, and analyzed.

Further, in one embodiment, once the biometrics device 35 scans the individual in question, the unique identification data is simultaneously sent by the program 110 to local, regional, and national databases 240-260 for bidirectional data access and transfer. Using artificial intelligence (e.g., neural networks), all relevant data as predefined by the program 110, is transferred automatically from the identified user's database 109, 250 (if the user is already in the system 100) to the local database 240 to assist with user profiling and analysis.

Once identification and authentication is performed, the program 110 will request that the individual end-user undergo a series of test questions for the purposes of creating a specific profile, which is in turn used to create a series of representative test cases. Existing metrics (including biometrics) would be incorporated into the system to establish an objective means to classify the diverse population of end-users into distinct sub-groups of users, with shared characteristics, which in turn map to computer-based technology preferences and biases. While the gamut of applications for the proposed invention is extremely large and diverse, (e.g., from a simple ATM to a complex CAD program), the concept remains consistent.

The test questions for the profiling system 100 may include the following components:
1) Intelligence: perceptual, cognitive, emotional;
2) Personality;
3) Emotional state: stress, affect, fatigue;
4) Computer experience;
5) Sensory and motor skills: hand-eye coordination, visual perception, auditory testing; and
6) Education and training.

Intelligence

Under the broad category of "intelligence", there are 3 sub-categories for consideration including cognitive, visual, and emotional intelligence. Each sub-category would have its own testing procedure to quantify an end-user's respective intelligent measure within that area. A number of existing tests are available to gauge these faculties, which could be incorporated into the program 110. Regardless of the intelligent testing mechanism being employed, the end-user's intelligence scores would be tabulated by the program 110 and used in the profiling process.

Examples of available tests that may be incorporated within the program 110 include (but are not limited to) the following:
1) Cognitive Intelligence Tests
   a) Wide Range Intelligence Test (WRIT)
   b) Reynolds Intellectual Assessment Scales
   c) Comprehensive Test of Nonverbal Intelligence (CTONI)
   d) Kaufman Brief Intelligent Test (KBIT-2)

2) Perceptual Intelligence Tests
   a) Johns Hopkins Perceptual Test
   b) Bender Visual Motor Gestalt test
   c) Woodcock Johnson Psycho-educational Battery
   d) Motor-free Visual Perception Test (MVPT-R)
3) Emotional Intelligence Tests
   a) Emotional Intelligence Appraisal (Bradberry and Greaves)
   b) Swinburne University Emotional Intelligence Test (SUEIT)
   c) Geneva Appraisal Questionnaire
   d) Emotional Intelligence Questionnaire (EiQu)

Accordingly, the user may be requested by the program 110 to take at least one of the above intelligence tests in at least one or more categories, and the information will be saved in the database 128, etc., and used by the program 110 to generate the test questions in determining the user profile.

Personality

Personality has been shown to have a dramatic influence on all aspects of everyday life and the manner in which an individual interacts with his/her environment. This interaction effect (between personality and end-user performance) also extends to technology, and different types of personality will show different biases and prejudices when it comes to new technology adoption. By classifying each individual end-user according to their own personality characteristics, a better understanding can be achieved as how to customize the technology in a manner befitting the end-users personality traits. By correlating these individual personality traits with those of the reference population (and associated auditing tool data), the computer program can be presented in a manner optimized to the individual user's personality characteristics.

Accordingly, the user may be requested to take one or more of a number of well-established personality tests which are currently available (or which may be later developed), which can be incorporated with the user's profiled data, and saved in the database 128 etc. Relevant examples of personality tests include (but are not limited to):
1) Myers-Briggs Type Indicator
2) Five-Factor Personality Model
3) Eysenck Personality Questionnaire
4) Oxford Capacity Analysis Personality Profiling of End-User Populations In addition to assessing each user's personality, the profiles across the end-user populations may be analyzed by the program 110. A number of personality profiling tests exist that can provide a reliable and reproducible means of stratifying populations of end-user into specific groups based on personality traits. The five basic dimensions (or factors) of personality that are tested in various personality tests include: Neuroticism, Extroversion, Openness, Agreeableness, and Conscientiousness. Various combinations of these major personality dimensions/factors provide insight into the major aspects of peoples' lives, by defining personality styles.

From the five majors factors of personality, one can derive important information about the way an end-user's willingness to explore new technologies and applications (i.e., Openness), ability to handle external stressors (i.e., Neuroticism), relative interest in group versus individual problem-solving and learning (i.e., Extroversion), self-discipline and organizational skills (i.e., Conscientiousness), and inherent trusting of outside informational sources (i.e., Agreeableness).

From the different types of personality styles, the program 110 can be structured to derive detailed information as to the interaction effects between the technology (i.e., computer application) and personality. Some examples of how the general population of end-users can also be stratified by the program 110, are as follows:

a. Style of Well-Being

This personality style can be divided into four broad categories, including gloomy pessimists, overly emotional, low-keyed, and upbeat optimists. The first two categories (gloomy pessimists and overly emotional) would be more susceptible to emotional swings and periodic distress (along with higher fluctuations in perceived stress levels). As a result, the program 110 may determine that those end-users fall may be better suited for technology applications that are more highly automated and require less manual direction, and present those options to those users. In addition, the incorporation of affective computing technologies by the program 110 into everyday workflow would allow for the immediate detection of higher stress levels (as measured by the program 110 of galvanic skin response or changing pulse/blood pressure). As objective measures of higher stress are detected by the program 110, the computer program could be adapted by the program 110 in a manner that has a calming effect to the end user—for example, simplification of the user interface, reprioritizing the work queue, or slowing down the navigational speed with which images are displayed (in cine mode), by the program 110.

b. Style of Defense

The four categories of this personality style include maladaptive, hypersensitive, hyposensitive, and adaptive. Hyposensitive individuals rarely experience strong negative affect (unlike the hypersensitive style) and as a result may be more prone to greater continuity and predictable workflow patterns. Adaptive individuals, on the other hand, are keenly aware of stress but typically use stress in a positive way, to stimulate creative adaptation.

As a result, the technology adapted to the hyposensitive or adaptive individual by the program 110 may allow for greater degrees of autonomy and creative adaptation, which may become of greater relevance in the interpretation of complex, cross-sectional imaging studies, such as CT or MR angiography.

Maladaptive and hypersensitive individuals are more negatively affected by stress and require technology adaptations by the program 110 that can simultaneously reduce stress and enhance performance. An example of this adaptation may be automated pre-processing and reconstructions of complex CT and MR studies by the program 110.

c. Style of Anger Control

Of the different styles of anger control, the most volatile would be the temperamental style, which is highly prone to stress and easily angered. As a result, the performance of these individuals can be dramatically impacted (in a negative manner) by fluctuations in perceived stress, that adversely effect performance (by deceasing workflow and diagnostic accuracy, while increasing cumulative fatigue). Technology adaptation for these individuals must be proactive in nature and incorporate "soothing" applications at the earliest signs of increasing stress. This could take the form of the program 110 providing mandatory time outs for the user, environmental controls (i.e., relaxing background music, adjustment (lowering) of ambient light, more ventilation/added cooling), and the use of automated decision support applications. Easy going personality styles would not be prone to anger and exhibit reduced emotional lability. As a result, these individuals would be less likely to experience significant changes in affect and stress and could perform at longer time intervals without interruption or changes in workflow.

d. Style of Impulse Control

The over-controlled personality style is prone to obsessive compulsive behavior and exhibits perfectionist strivings. As a result, diagnostic accuracy is of paramount importance and these individuals will in all likelihood use more time-consuming and complex technologies to achieve this goal. More frequent use of workstation tools, manual processing techniques, and greater access to data by the program 110 may become a dominant feature of this personality style. As a result, the adaptive technology program 110 must not only provide greater functionality to this specific type of end-user but also anticipate these needs "before the fact", in order to simultaneously enhance workflow/productivity, while also decreasing cumulative fatigue and stress caused by manual deployment by the end-user.

The opposite personality style (to the over-controlled style) would be that of the relaxed personality style. This type of individual would see little need to exert rigorous control over their behavior and look for the "easy way". As a result, the technology adaptation for this personality style by the program 110 would be less "hands on" and instead provide automated workflow. This can be done by creating automated hanging protocols and navigation, specifically designed to the modality, anatomic region, and clinical indication being evaluated.

In one example, a relaxed personality style radiologist interprets an abdominal CT exam to evaluate suspected appendicitis. Based on the modality (CT), anatomic region (abdomen), organ system (gastrointestinal), and clinical indication (rule out appendicitis); there would be a designed automated template that would be created by the program 110, that provides a specific hanging protocol, navigational mode, workstation tool palette, and decision support. The relaxed radiologist could in this instance elect to use the "automated template" offered by the program 110 in a manner similar to a player piano that essentially works on autopilot. Any manual changes in workflow directed by the relaxed radiologist would be recorded by the program 110 and automatically incorporated into the new default template by the program 110 for that anatomic region, modality, and clinical indication. This provides a means for the program 110 to simultaneously adapt technology to both the end-user's personality and clinical preferences.

e. Style of Interests

Within the various categories of personality styles within this group are mainstream consumers, creative interactors, homebodies, and introspectors. This personality style is of particular interest to the present invention and any technology applications inherent to reporting/communication. Traditional reporting of medical imaging studies consists of radiologist-produced unstructured text which is input by speech, which is then transcribed using either speech recognition software or external transcriptionists. In either mode, the text prose reports that result are entered into the picture archival and communication system (PACS), radiology information system (RIS), and electronic medical record (EMR) for clinician review.

With the advent of new computer-based imaging and information system technologies, additional functionality exists that can dramatically enhance the reporting/communication process. One manner of doing so is through electronic linkage of pertinent medical images (with annotated findings) by the program 110 into the text report through the use of hypertext links. This direct embedding of "key images" into the report by the program 110 provides a means to communicate pertinent findings with direct visualization. The ability to electronically integrate data into the report, as is conducted by the program 110, is not restricted to images alone, but also provides a means with which the authoring radiologist can incorporate additional data points pertinent to the imaging findings, apart from the images. These additional data can include (but is not limited to) anatomic atlases, journal articles, differential diagnoses, teaching files, and websites.

In the radiology context, the program 110 can conduct medical reporting through the creation of structured text reports which utilize a standardized medical lexicon. This will foster the creation of referenceable databases which can be used for trending, clinical outcomes, and utilization analyses. In addition, structured reporting has the potential to dramatically reduce (and even eliminate) much of the ambiguity and uncertainty which currently exists within traditional text prose reporting.

In addition to these enhanced reporting capabilities, the program 110 of the present invention creates the ability to automate the communication of clinically unexpected and emergent findings through user-specific communication pathways such as auto-faxing, text paging, and e-mail alerts to referring clinicians. The program 110 provides an effective means with which the authoring physicians (in this case radiologists) can integrate disparate data sources into a single, comprehensive report and instantaneously communicate pertinent findings with an electronic auditing trail for receipt confirmation.

By understanding the personality traits of the end-user population, the program 110 can adapt the computer programs used in a manner to maximize compliance, workflow, and overall satisfaction.

Creative interactors have interests that revolve around the new and different and like to share their discoveries with others. Mainstream consumers, on the other hand, have simpler interests that tend to be traditional and follow the mainstream. These two different personality styles naturally lend themselves to different adaptations of reporting/communication styles by the program 110. Whereas the creative interactor would prefer to take on a more proactive teaching role, the mainstream consumer prefers a more passive approach, allowing the program 110 to be the driver. The creative interactor may desire to create customized bookmarks of web-based resources using the program 110 to manually incorporate into the multi-media report, while the mainstream consumer prefers to have automated program 110 generated templates serve as the reporting platform.

In one embodiment, the personality traits and preferences of a referring clinician in a medical application can be considered by the program 110 when constructing a medical reports. If, for example, a referring clinician profile is maintained within the PACS/EMR database and presented to the radiologist by the program 110 prior to report generation, then a customized report (in style, format, and content), can be constructed by the program 110 in keeping with the expectations of the clinician.

If artificial intelligence techniques are further integrated into the reporting process of the program 110, then different versions of the same report (as well as the preferred communication pathways) can be generated by the program 110, based on the different personality profiles and preferences of the clinicians receiving reports. This is of particular interest when multiple clinicians are involved in the care of a single patient.

f. Style of Activity

The different styles of activity include fun lovers, go-getters, lethargic, and plodders. Fun lovers tend to be highly energetic, spontaneous, and impulsive. Go-getters tend to be highly efficient and work at a rapid tempo. Plodders tend to be methodical in their work, concentrating on the task at hand, and working slowly and steadily until the job is completed in its entirety. One can see how adapting different versions of decision support technology can have a dramatic and profound impact on end-user performance, according to their respective personality style.

Decision support tools take on many different forms and can include artificial intelligence techniques (e.g., neural networks), computer-aided detection (CAD), automated differential diagnosis, textual analysis, and automated quantified analysis.

If, for example, three different radiologists are interpreting a screening chest CT (in the evaluation of lung cancer), they may have far different workflow patterns and expectations of themselves and the computer technologies they are using. The go-getter is primarily focused on maximizing productivity and in doing so, elects to utilize CAD software (for the detection of lung nodules) prospectively, in essence providing a first-pass interpretation using the program 110. The go-getter would then begin the process of image review and interpretation based on the CAD preliminary analysis. The go-getter can also have the program 110 preset to display the CT images after applying the CAD mark-up. This provides the radiologist with a set of "pre-read" images, thereby decreasing their own time spent in image review and interpretation.

The plodder prefers an entirely different manner of workflow for image display, review, and interpretation. The plodder is less concerned with throughput and more concerned with diagnostic accuracy. The plodder elects to review the entire imaging dataset presented by the program 110 a priori, before applying the CAD analysis. In doing so, he/she relies more on their own interpretation then the program's, and uses the CAD program merely as a check for missed findings. The plodder would elect to have the CAD applied manually (only under their control), and only after they have completed their own comprehensive analysis.

The fun lover may find himself easily distracted over the course of a long work day and begin to experience progressive levels of fatigue as the day progresses. As a result, the fun lover may elect to have the program 110 display serial exams in pre-defined time intervals (which may be variable dependent upon exam type, complexity, size, and indication). By doing so, the fun lover compensates for their own tendency to be distracted and allows the program 110 to become the task master of sorts, and introduce greater order and discipline to the workflow. In addition, the fun lover may identify specific imaging findings that call for further analysis and request the program 110 to perform these measurements in an automated fashion.

One example would be the same screening chest CT (for lung cancer). Upon identification of a lung nodule or mass (by either the radiologist or CAD program), the program 110 would be instructed to automatically obtain linear, volumetric, and density measurements.

All of these personality-driven computer adaptations are further modified in accordance with changes in affect and stress by the program 110, which are objectively tracked in real-time through the use of affective computing technologies. If for example, the go-getter is reaching unacceptable levels of stress as determined by the program 110 (e.g., as determined by changing blood pressure), the CAD application may be delayed by the program 110 accordingly, for a short period of time (e.g., 10 seconds), thereby forcing him/her to reduce their speed. If the plodder is working too slowly (relative to program 110 timed analysis based on their own specific profile), the program 110 may provide an alert to the radiologist with a prompt asking them if they want to modify the workflow to enhance throughput. This modified workflow can take many forms from providing CAD analysis on the "front end" to increasing the navigational speed on cine image display.

g. Style of Attitudes

The different styles of attitudes tend to correlate with previous studies in how different types of individuals adopt new technologies. Progressives tend to be open-minded, believe in innovation, and willing to try new solutions. Traditionalists tend to be reluctant to adopt new technology and reticent to change. Free thinkers are critical thinkers who like to form their own judgment based on fact.

The manner in which technology upgrades are incorporated into the program 110 may be in part dependent upon attitudinal style. A new software upgrade may be quickly embraced by the progressive, who when provided with the opportunity to "upgrade" will immediately opt in. The progressive end-user would be more apt to utilize educational wizards and electronic teaching modules provided by the program 110 to incorporate the new technology into existing workflow. The traditionalist would reject most attempts to "upgrade" and prefer to stick with the "tried and true". An improved technology application would have to be gradually and systemically introduced into the workflow by the program 110 in order to gain acceptance by the traditionalist. The free thinker would expect some sort of objective evidence (which may take the form of scientifically collected data) before adopting new or upgraded technology. In the end, the program 110 will have the flexibility to adapt to the personality profile differences in order to ensure compliance.

In an exemplary embodiment, decision support applications for the interpretation of a chest CT by a radiologist, can be implemented by the program 110 to accommodate differences in the personality of the user.

For example, due to unique differences in personality, one would expect differences in workflow with respect to end-users as it relates to "go getters", "lethargies" and "plodders".

"Go getters" tend to work with an internal time clock driving them to maximize their productivity. As a result, they often look for new and creative means to streamline the interpretation process and incorporate "short cuts" whenever possible. They tend to prefer automated over manual workflow and are receptive to computer-driven decision support technologies, if they have been proven to have acceptable levels of diagnostic accuracy and can be automatically integrated into workflow without additional time delays or manual prompts. As a result, the personality profile of this group may request a program 110 driven workflow.

The modus operandi of the "go getter" is to synergistically maximize accuracy and productivity and accomplishes this by leveraging computer automation whenever possible. As new computer functionality and automation is incorporated into the program 110, automatic e-mail alerts are sent by the program 110 to the "go getter" who then has the option to automatically incorporate these advances into his/her pre-defined workflow algorithm. The program 110 can also use the auditing tool database 128 etc. to identify more successful users' workflow (within each personality profile category) and integrate this workflow into automated templates (as previously described), which can be offered to other users within the corresponding personality/technology profile group.

In the case of the "plodders", who are more methodical and deliberately slower than their "go getter" counterparts, they are less inclined to utilize automated CAD and workflow software programs, and instead rely on manual display, navigation, interpretation, and reporting strategies. When automated programs such as CAD are utilized by "plodders", they are typically applied only after a complete and thorough manual review (which is eschewed by the "go getter"). Any program 110 designed for the "plodder" takes into account these significant differences in workflow expectations and focus on consistency, reproducibility, and greater access to stored data. In addition, "plodders" may prefer to review the imaging dataset in multiple planes and reconstruction algorithms for enhanced diagnosis. The auditing tool of the program 110 (discussed further below) provides a means to objectively determine these additional requirements (based on type of exam, anatomic region, and clinical indication) and incorporate these modifications directly into automated display/presentation templates.

One example of this expectation for enhanced data access in the radiology field, would include the retrieval of a greater number and diversity of imaging studies for correlation and comparison at the time of diagnosis by the program 110. The "plodder" may require retrieval of multiple comparison CT exams (not just the most recent), as well as other imaging studies of the chest (e.g., chest radiography) by the program.

In addition, the plodder radiologist may want greater access to clinical data contained within the EMR, such as past medical history, prior surgeries, risk factors (e.g., smoking history), and demographic information. By reviewing the auditing data, the program 110 can be developed to provide user profiles that incorporate these additional data access requirements and provide automated options for additional data integration.

In addition to a preference of manual navigation and interpretation protocols, "plodders" may also demonstrate a preference for direct communication of clinically significant findings to clinicians (as opposed to automated delivery methods by the program 110, preferred by "go getters"). The program 110 can facilitate this altered workflow by incorporating clinician profiles into the "plodder" radiologist reporting/communication package. By reviewing this computer-generated clinician profile, the "plodder" radiologist can identify the communication preference of each individual clinician (e.g., text paging, cell phone, etc.) and efficiently communicate it without unnecessary delays.

"Lethargics" create different and unique challenges that are less focused on workflow, and more focused on consistency. While the "go getter" is at one extreme for productivity and workflow, the "lethargic" is at the other. The program 110 which is designed to accommodate for "lethargic" users may need to incorporate visual and auditory timing cues, to alert the user as to delays in workflow. A supervisor (or department chief) may incorporate time expectations for different tasks into the program 110 (i.e., in the radiology field, including task times based on a number of variables such as anatomic region, clinical indication, exam modality, exam size and complexity), and the program 110 may provide direct feedback to the user when this time allocation is exceeded. At the same time, when user productivity begins to lag, the program 110 may be directed to default to automated, as opposed to manual workflow. In order to ensure that "lethargies" are not sacrificing accuracy for productivity, the program 110 ensures that the imaging dataset is reviewed in its entirety (i.e., no images missed), before allowing the "lethargic" user to proceed onto the next exam. In a similar manner, "lethargies" may also be required by the program 110 to review pertinent historic comparison data. Visual prompts and automated reminders provided by the program 110 may serve the useful purpose of facilitating workflow and improving performance of this personality profile group. Software upgrades and educational tools can be directed by comprehensive data analysis from the larger population of end users that fall into this category.

Emotional State

Both subjective and objective measurements can be recorded in evaluation of an end-user's emotional state, which is dynamic and constantly changes over time. As a result of this continual change, frequent and repetitive measurements of one's emotional state are essential, particularly in the performance of time-intensive and/or repetitive tasks, where cumulative stress and fatigue lead to performance degradation. Currently available means to measure these variables include:

1) Stress
   a) Perceived Stress Scale (PSS)
   b) Perceived Stress Questionnaire (PSQ)
2) Affect
   a) Physiologic measurements (i.e., pulse, blood pressure, galvanic skin response)
   b) Facial expression recognition software
3) Fatigue
   a) Fatigue Assessment Scale (FAS)
   b) Facial expression recognition software
   c) Digit Vigilance test In addition to altering end-user's performance, changes in one's emotional state can also impact the user's own preferences and requirements for computer optimization. As an example, when the user's stress levels reach a critical threshold, the workstation tools uses, navigation speed, or font size may require adjustment for optimized performance. At the same time, progressive levels of fatigue may alter attentiveness and necessitate alterations in the user interface or presentation state to ensure adequate performance. The end result is that unlike other profile variables which are largely static in nature, emotional state is constantly changing and requires frequent alterations by the program 110 (in reaction to the end-user's emotional state), to ensure adequate performance and well-being of the user.

The biometrics input means 35 may be used to measure emotional state, and may encompass the varying equipment necessary to evaluate stress, affect and fatigue levels. For example, a camera 35 may be used to take photographs of the user in order to analyze changes in facial expression which will show stress or fatigue (i.e., furrowing of brows or drooping of eyelids, respectively), or sensors 35 may be attached to the user to measure blood pressure or galvanic skin response etc. for affect. Any external equipment, such as sensors 35, or a camera 35, would be connected to the client 101, and would be in as unobtrusive a manner such that the user may utilize the client 101 without undue interference.

In one example, an "overly emotional" radiologist who is tasked with the interpretation of a chest CT angiographic exam, for the clinical indication of pulmonary embolism (i.e., blood clot), would be determined by the program 110 to have a personality style that calls for a higher degree of automated protocols. Thus, the images from this CT exam would be displayed by the program 110 using a pre-defined hanging protocol (based on the exam type, anatomic region, and clinical indication) and with a predetermined display format. The navigational format (which among other things, specifies the manner and speed at which the images are sequentially displayed), are also automated based on a similar pre-defined protocol by the program 110. The user interface and menu of workstation tools available to the radiologist for image manipulation and measurement are also instituted by the program 110 to best suit the individual radiologist (based on experience, training, historical performance) for that specific exam type and clinical indication.

In one example, a radiologist is reading and interpreting a number of chest CT angiographic exams. Before the radiologist begins each individual reading session, he/she is presented with a 12-point item, for example, a multiple choice questionnaire, provided by the program 110, to quantify perceived (baseline) stress levels. This perceived stress is supplemented by continuous objective stress levels taken by the program 110 using the peripheral equipment hooked up to the client 101, which can be calculated through a variety of affective computing measures (e.g., galvanic skin response, blood pressure, pulse, facial expressions etc.). The combined perceived and measured stress indicators are in turn used by the program 110 to identify critical thresholds of stress, which in turn makes the program 110 produce changes in technology and workflow.

Continuing the example, the radiologist interpreting the chest CT angiographic study in the morning (i.e., at 10:00 am) is relatively fresh and well rested. Based on the initial stress measurements taken by the program 110, a low level of stress is determined (relative to the radiologist's cumulative baseline) by the program 110.

As a result, the tool bar, user interface, and navigational speed are all presented by the program 110 in a form commensurate with the individual's personality profile at "low stress". Several hours later (i.e., 3:30 pm), the same radiologist is presented with a similar exam type but under different stress conditions by the program 110. The affective computing measures of the program 110 have determined that this same radiologist is now under "high" levels of stress (based on that individual radiologist's baseline). Once sequential high levels of stress are recorded, the computer software program is automatically adjusted by the program 110 to include simplification of the tool bar, reformatting of the user interface, and reducing image navigational speed, among others. If continuously program 110 monitored stress levels continue to rise to reach pre-defined "critical" levels, an automated computer time-out is generated by the program 110, which prevents the radiologist from continuing until measures stress levels have been reduced below "critical" levels.

Computer Experience

Whereas intelligence and personality remain essentially fixed over time and emotional state is constantly changing; computer experience is a slow, evolving process; which is highly dependent upon each individual end-user's motivation, adaptability, and personal/professional interest. While some end-users have a nature proclivity for computer skills, others are less interested and often intimidated by changing technology. Regardless of each individual's native skills and knowledge, computer experience is acquired and as any acquired skill provides the recipient with capabilities not shared by less experienced peers.

Not all computer experience is equivalent and as a result, the specific application being evaluated must take into account experience that is specifically relevant to the task at hand. Certain computer skill sets and experience are often translatable to a wide range of other computer-related tasks and as a result, provide the respective end-user with relevant experience to apply to the new task being evaluated. Many video games, for example, improve visual perception, motor skills (hand-eye coordination), and problem solving and as a result may translate into practical experience in a new task, such as computer graphics and design. Other skills, for example, slideshow presentation programs are specialized and would be relevant for the end-user using a computer graphics/design program, but irrelevant to a task-specific program such as on-line scheduling.

In the present invention, user-specific computer experience would be quantified through a questionnaire displayed by the program 110, that would identify both general and task-specific computer skills and creates a quantifiable score relative to the specific computer program being analyzed. This score can in turn be periodically updated and modified as each end-user gains relevant computer experience. The customization of the specific program would take each end-user's computer experience into account, along with the other variables denoted in the profiling system 100 (i.e., emotional state, intelligence, etc.).

On a very simplistic level, variations of each computer program or technology accessed by the user can be developed on a hierarchical scale of "simple" to "complex" by the program 110. The "simple" program or technology would utilize the most basic (and least numerous) computer tools, user interface, input device, and navigation, etc. provided by the program 110, and the "complex" program may utilize more advanced tools by the program 110, including alternative input devices, and 3-D display and navigation etc.

Sensory and Motor Skills

Fine motor skills (i.e., hand-eye coordination) are a fundamental component of computer-related tasks. Depending upon the individual aptitude of the end-user and differential motor skills, the specific type of input device and navigational strategies may vary. While most computer users traditionally use a computer mouse or keyboard for input, a number of alternative input devices exist, (i.e., voice commands, foot pedals, electronic stylus) which the program 110 may use for end-users who require the utilization of different motor skills.

Examples of tests to assess hand-eye coordination include (but are not limited to)
1) Test of Visual-Motor Skills (TVMS-UL)
2) Bender Visual-Motor Gestalt Test
3) Wide Range Assessment of Visual Motor Ability (WRAVMA)

In addition to motor skills, visual perception skills are also an essential component to computer operation and are of particular importance to those computer-related tasks where spatial and contrast resolution are important attributes (i.e., evaluation of medical images). The optimized manner in which computer data (i.e., icons, text, or graphics) is displayed is largely dependent upon the end-user's visual perception skills and is therefore an integral component of the assessment and analysis performed by the program 110.

Examples of tests to assess visual perception include (but not limited to)
1) Motor-Free Visual Perception Test-Vertical (MVPT-V)
2) Test of Visual-Motor Skills, Revised (TVMS-R)
3) Test of Visual-Perceptual Skills (non-motor) (TVPS-3)

Another sensory skill which may have relevance to computer software design is auditory skills. If the program 110 integrates sound into its design, then the end-user's ability to discriminate sounds at different frequencies is essential to operation. At the same time, if one has to compensate for poor skills in one area (e.g., visual), then another skill set (e.g., auditory) may be used by the program 110 in maintaining operability for that individual end-user.

The program 110 of the present invention could test the individual end-user for motor, visual perception, and auditory skills prior to customization of the user profile. These tests could be performed using the input means 104 associated with the client (i.e., microphone in display 102, mouse, joystick etc.). Once the individual end-user's sensory/motor profile is established and the data saved in the database 128 etc., then the computer application is altered by the program 110 to take advantage of those intrinsic skills most developed in that individual. In addition, computerized education and training programs can be identified by the program 110 to assist the individual end-user with those skills deemed essential to computer usage, but currently deficient. An example would be computerized simulation programs used to improve hand-eye coordination and technical skills for surgeons in the training of new operative procedures.

Education & Training

Professional education and training is an integral component of an end-user's profile. For generalized computer tasks (i.e., internet surfing, or using a GPS system), educational background is of limited utility. However, for more specialized computer tasks (i.e., airline operator control, architectural design), one's professional education and training is a critical component to customization of the software program. Similar to computer experience, education and training experience is also a variable that evolves over time and must therefore be re-evaluated at periodic intervals within the profiling system.

Setting User Profiles

Figure 2:
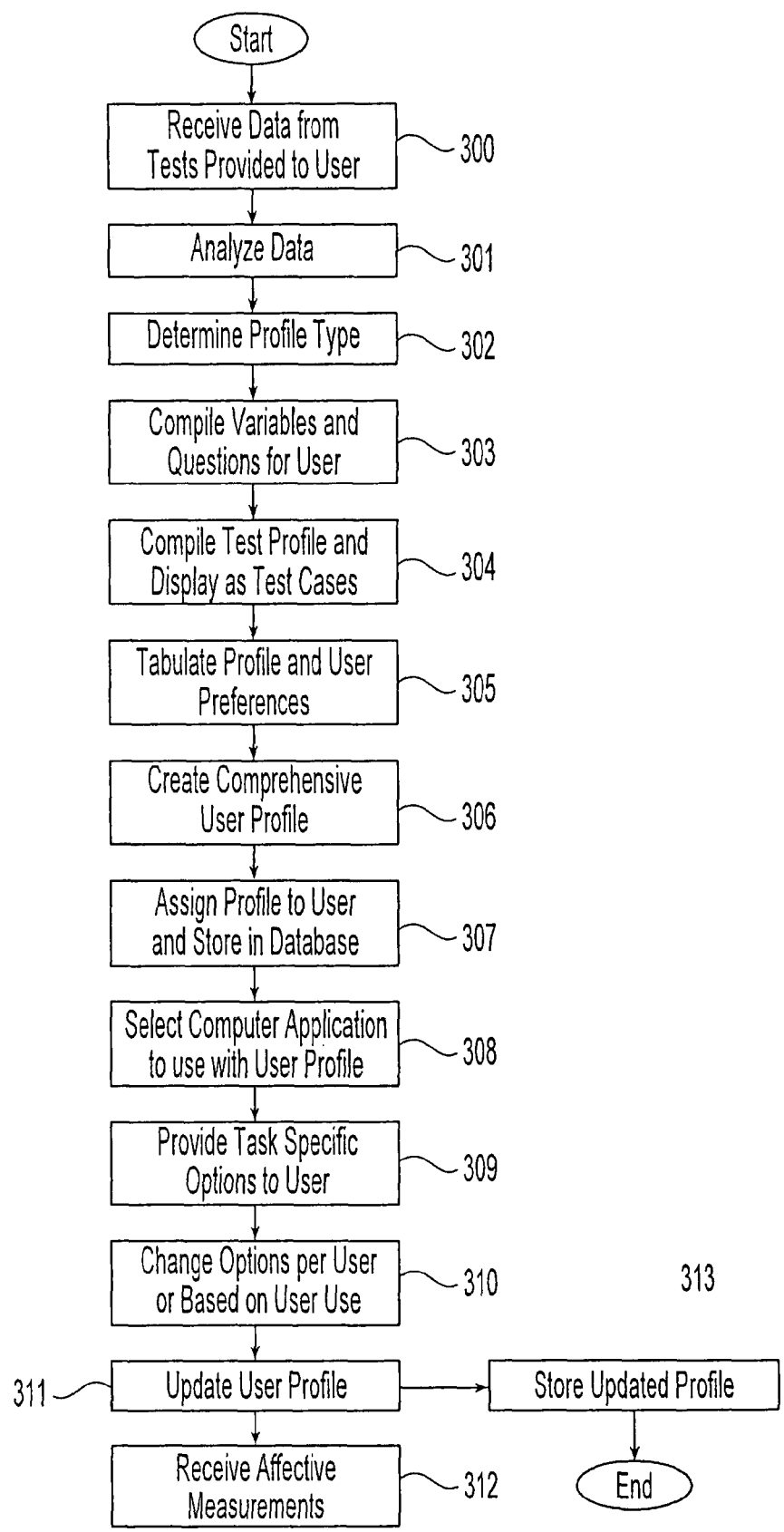
FIG. 2 shows a flowchart of the dynamic profiling system according to one embodiment consistent with the present invention.

After at least one or more of the above tests are performed by the user in step 300 (see FIG. 2), the program 110 will analyze the various data provided in step 301, determine the type of user profile that may encompass the user's abilities and the type of interaction sought in step 302, and then automatically compile a list of variables and a list of questions to present to the user in step 303. Thus, the end result is a computer-based profile testing system 100, which is displayed for the user as test cases in step 304.

The end-user reviews the test cases (in a manner similar to the way a patient reviews different visual presentation states when tested by an optometrist), and selects from a series of options, their own unique preferences. These "profile and individual specific" preferences and results are tabulated by the program 110 in step 305, which then creates a comprehensive user profile based on the reference database in step 306. The profile generates is then assigned to that specific end-user and stored in a database 128 etc. for future use in step 307.

Specifically, each time that end-user signs into the computer system 100 (using biometrics for authentication and identification), their profile, if already stored, is automatically retrieved by the program 110 from the master database 128, for example, and the retrieved specific set of parameters is applied to the computer program being used.

Accordingly, once the user confirms their identity, and once the program 110 authenticates it, the user may set their profile, and then select the specific computer application to be used in step 308.

Depending upon the specific computer application being used, the profiling data would present different task-specific technology options to the end-user in step 309. The complexity of the profiling data and customization options available to the end-user would obviously be different depending upon the computer application and task at hand. Further, the user may change those options as they proceed with the program, or over time in step 310.

An example of a complex operation would be the interpretation of digital medical images by a radiologist, while an example of a simpler operation would be creating a text-based document using a word processing software program. The common theme is that the computer-based program is the same for all users, but the manner in which the computer program is presented for operation is different, depending upon the profile characteristics of the end-user.

This customization (based on end-user profiling) can take a number of forms and cover the fill spectrum of individual processes and steps an end-user goes through in their computer interaction. For the example of the radiologist who is tasked with rendering an interpretation on a medical imaging exam (e.g., CT) this customization by the program 110 would include the user interface, workstation tools, navigation, input device, image presentation state, analysis, and reporting. For a less specialized task such as surfing the Internet, the customization by the program 110 would also include the user interface, input method, computer-based tools and presentation state; along with search engine strategies and educational resources.

Further, at predefined periodic intervals (or when designated by the individual end-user), the profiling sequence will be repeated by the program 110 to update the end-user's profiling parameters in step 311. This is of particular importance to those profiling variables that are more prone to temporal change, such as computer experience, education, and training.

In addition, during the course of a prolonged and time-intensive application (e.g., series of medical image interpretations by a radiologist), the program 110 may provide additional capabilities of modifying the application in real-time, based on updated data inputs from the end-user (e.g., affective measures related to stress or fatigue etc.) in step 312.

Each updated profile is stored by the program 110 in step 313, a master database 128 etc. that is uniquely tied to the biometrics signature of each end-user. Technology developers can access anonymized data from these databases 128 etc. for future technology development and upgrades, by analyzing the usage of varying groups of users. Further, users may be able to put their user profiles on a portable chip for installation in any device, or access them over the internet. Further, users may be able to grant full or fractional access to other users or to third parties (i.e., marketing companies, family members, shopping registries, etc.), along with the use of privacy and security safeguards intact (i.e., varying levels of access). Still further, user profiles could be meshed with professional profiles for better service to customers (i.e., investment advisor).

Auditing Tool

Once the profiling has been completed on each individual end-user, an electronic auditing tool embedded within the program 110 prospectively tracks all computer functions and commands executed by each individual end-user. The auditing tool is similar to that described in copending U.S. patent application Ser. Nos. 11/699,348, 11/699,349, 11/699,350, 11/699,344, and 11/699,351, all filed Jan. 30, 2007, and U.S. patent application Ser. No. 11/586,580, filed Oct. 26, 2007, the contents of all of which are herein incorporated by reference.

This auditing tool of the program 110 allows for automatic data collection on how each individual end-user interacts with the computer program including (but not limited to) the various computer functions and workstation tools utilized for each individual task performed; in effect, creating user and task-specific statistical patterns of utilization. This automated data collection can be collected and analyzed by the program 110 relative to specific individual users, peer groups, or computerized programs to determine common and unique actions inherent to different profile groups within a given computer program.

By tracking cumulative data on multiple users within different profile groups, information can be gleaned as to specific tendencies different profile groups have in their interaction with different computer applications and tasks. By understanding these "profile specific" computer tendencies, the program 110 can be tailored in individual applications to the inherent strengths and preferences of individual users.

At the same time, the auditing tool data can be used by the program 110 to identify the most efficient end-users within different profile groups to create "optimization" or "best practice" templates, which can be used as educational and product development templates within different profile groups.

For example, taking a heterogeneous population of end-users using a computerized program such as an electronic medical record (EMR), the profiles implemented by the program 110 would follow the above sequence of questionnaires and testing, and would be created accordingly to include a number of different variables. In the example, a sub-population of users, which are all internal medicine practitioners within a single hospital, review their patients' medical information (i.e., lab work, consultation notes, imaging data) on the EMR. In the sub-group, there are 32 different internists, which fall into 5 major profile groupings as defined by the program 110, based on their collective intelligence, personality, sensory/motor skills, emotional state, and computer experience. Within the first sub-group are 7 different internists, all of which have basic computer skills as compiled by the program 110. As auditing tool data is collected and analyzed by the program 110, it is determined by the program 110 that within this group of 7 internists, one in particular (Dr. Jones), has a tendency to review lab data in the most efficient fashion, by using several short-cuts that many of the other internists do not use. The auditing tool data of the program 110 provides the objective data to identify the most efficient use by a user, and to incorporate the various steps and tools used by the user, into standardized templates and educational tools (in the form of an electronic wizard) for all users within each different profile group. The program 110 will modify the standardized templates for each different profile group, in light of the intrinsic differences each group possesses, in terms of education/training, computer experience, intelligence, personality, sensory/motor skills, and affect. Thus, the auditing tool data compiled by the program 110 provides an alternative means of profiling users, and can track when an individual user begins to deviate from their natural pattern of use. This can be a potential harbinger of change in workflow etc., with the user's changes (as determined by the auditing tool) pointing out potential areas of concern with an individual end-user's computer usage. As previously stated, certain profile variables are subject to periodic change (i.e., emotional state, computer experience) and the changes identified in workflow by the program 110 may to some extent serve as a predictor of a user's changing profile.

Because each individual end-user's emotional state is constantly changing, the auditing tool of the program 110 can serve as a vital source of objective feedback, as to how emotional state affects workflow. Once an individual user's workflow pattern for a specific computer program is established (through auditing tool data), then that user's own change in workflow can be used to provide direct feedback to the end-user, in the event that prospective workflow is dramatically changing.

For example, if we use the internist reviewing medical data on the EMR, workflow changes throughout the course of the day based on the time of day, volume of work, emotional state at the time, and specific task being performed. If, in the example, Dr. Jones is reviewing lab data and is performing additional steps requiring significantly more time than is customary for his standard practice, the auditing tool of the program 110 may be able to provide real-time feedback to Dr. Jones of the deviation from his standard practice. Dr. Jones would then be given the option by the program 110 to continue "as is" or have the program 110 make automated modifications, to maintain Dr. Jones' "standard" workflow. This can take the form of automated templates stored within the databases 128, etc., based on Dr. Jones' auditing history.

Bi-Directional Feedback

The program 110 of the present invention is adaptive, and may be continuously monitored and refined, based on the specific needs and patterns of use by the diverse community of end-users. The integration of the electronic auditing tool with user group profiling, allows for dynamic and continuous data collection and analysis of how different user groups interact with the specific computer program being evaluated and the different points of failure or relative disuse.

Thus, the cumulative data from the auditing tool and user profile groups may be used by the program 110 to identify "best practice" patterns within different profile groups, inter-group variability and commonality, and workflow bottlenecks. This data can in turn be used by the program 110 to enhance product development, which is customized to the unique and different needs of each different user profile group.

In addition to the objective workflow data (as described in corresponding U.S. patent application Ser. No. 11/586,580), affective computing measurements (e.g., pulse, facial expressions) tracked by the program 110 of the present invention, can provide additional data as to how different user's emotional states change over time and how emotional state and workflow are inter-related.

If for example, a specific user experiences heightened anxiety and stress with a specific function each time he/she encounters it, then the combined auditing tool and affective computing data as analyzed by the program 110, will highlight this relationship and provide the user or overseer, objective data for intervention. This may lead to a recommended modification in the program 110 or individual user's workflow (via an electronic wizard instituted by the program 110).

As the different strategies are employed, the data will be collected and compared by the program 110 to investigate whether the recommended intervention was successful in improving workflow and/or reducing stress. In effect, the program 110 creates a bi-directional feedback loop between the individual end-user, computer program, entire population of end-users, and program developers.

Just as the developers can identify points of failure, stress, and bottlenecks, the individual users can make recommendations for product improvement through the bi-directional electronic wizard program 110 that makes recommendations for enhanced performance. In this case, each individual user would be asked by the program 110 to undergo the personality and technology profile questionnaires, prior to being assigned a password. Based on the profile established by the program 110, the user would be "matched" by the program 110 with similar user profiles within the comprehensive database.

Auditing tool data collected by the program 110 would be analyzed on individual, group, enterprise-wide, and/or community-wide bases, with feedback provided to each individual by the program 110 on a regular interval (e.g., monthly) as to changes in workflow/productivity based on their own historical records. In addition, the user would have the opportunity to provide specific input as to perceived deficiencies and recommended modifications to existing programs. These end-user recommendations can be tracked and analyzed by the program 110 relative to their profile groups to identify similarities in preferences, which can be used in continuous product refinement.

Education & Training

Different users assimilate new information in a variety of ways. Some users prefer "in person" education, which can take the form of "hands on" workshops, formalized one-on-one training, or less formal peer to peer education. Others prefer self-teaching which can be accomplished through manuals, exploration (trial and error), or electronic teaching modules. Educational preferences are tied to multiple variables including personality, computer experience and comfort, and educational background. While personality is an important predictor in educational preferences and biases, the ability to track individual workflow with an electronic auditing tool, as described in corresponding U.S. patent application Ser. No. 11/586,580, provides objective data feedback as to how these different user profile groups interact with technology.

In addition, the frequency and manner in which educational materials are presented by the program 110 are largely dependent upon each individual user's unique workflow. Personality profiling by the program 110 provides insight as to how different groups within the community at large learn and interact with technology, while auditing tool data (and the derived functionality quotient) compiled by the program 110, provides valuable data as to how individual users (within different personality profiles) can be more efficiently educated and trained, based on their individual workflow habits.

As workflow data is collected and analyzed by the program 110, numerous options are provided to the user by the program 110, for accessing the feedback and educational programs. In one embodiment, the program 110 acts as an electronic wizard, which can appear as a pop-up whenever workflow is interrupted (bottleneck) or unexplainably slowed as compared to a preset (stored) sequence or timing. As new product refinements are integrated into the program 110, the program 110 may offer the end-user an on-line tutorial or references for further education and training—either automatically, or upon an affirmative decision by the user.

Electronic educational aids can be customized to each individual end-user's profile, performance goals, and educational preferences by the program 110. The success of these educational aids can be directly tied back to objective auditing tool data, where the program 110 can track workflow "before and after" the educational intervention and provide this feedback to the end-user. If users within the same profile group have demonstrated improved educational gains and workflow efficiency as determined by the program 110, the educational strategy utilized may also be applied to other end-users within the profile group, with the expectation that similar profiles will act (and learn) in similar fashions.

Note that although all of the above features of the present invention have been described as being utilized, one of ordinary skill in the art would recognize that only one or more of the various parameters may be gauged by the program for compiling the end-user profile. Further, even though the program 110 is described as performing the above functions, compilations and analysis automatically, or in accordance with the user's affirmative actions, the user may be provided with the option to turn "on" or "off" any of the above functions as desired (i.e., education and training, etc.).

Examples of User Profiles

The apparatus and method of adapting computer-based systems to end-user profiles of the present invention, can be used by a diverse group of end-users, in a wide variety of applications. Essentially any computer program or application can be adapted to the adaptation process of the present invention, with the unique attributes and preferences integrated into the display and workflow. Those applications, which are highly technical and specialized in nature (e.g., EMR), will depend on the profile variables discussed previously. More simplistic and less specialized computer applications (e.g., word processing) will tend to focus more on personality and emotional state and less on different intelligence factors and sensory/motor skills. The end result is that each of the profile variables will have varying degrees of importance, depending upon the specific attributes and technical requirements of the application in question.

In one exemplary embodiment, User A is a highly intelligent 44 year-old male professional, with limited computer experience, a pessimist, with a high level of anxiety, and modest sensory/motor skills without physical impairment.

Figure 3:
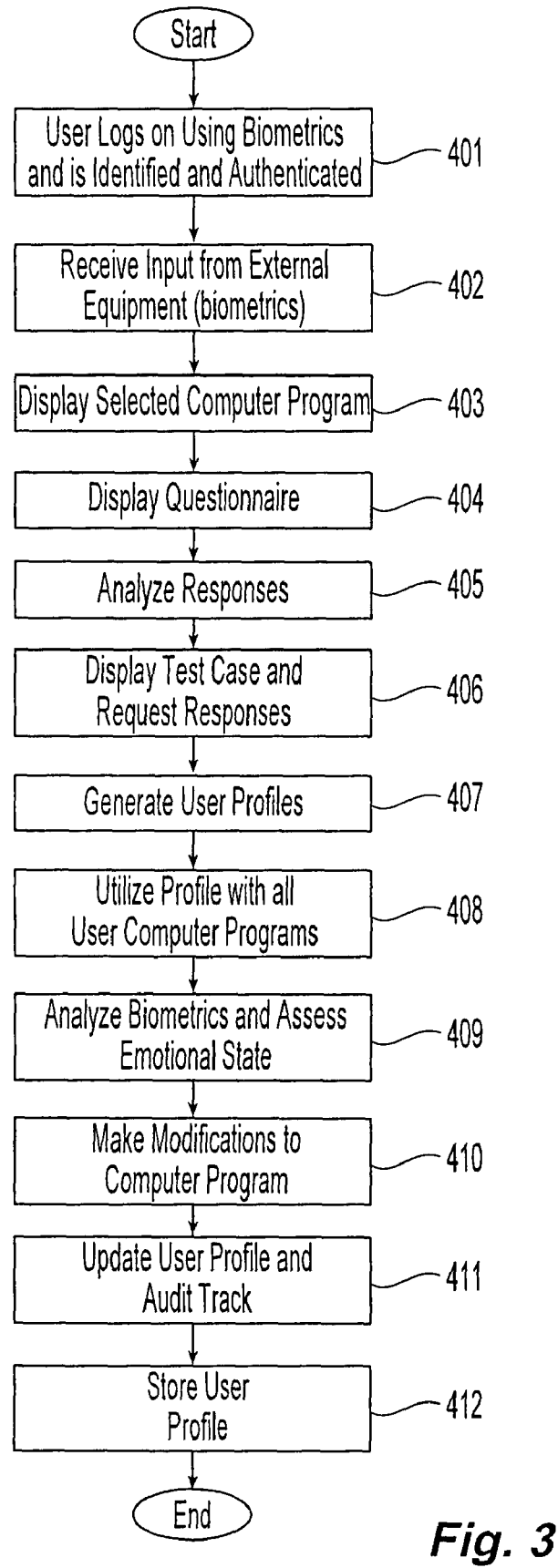
FIG. 3 shows a flowchart of the dynamic profiling system according to another embodiment consistent with the present invention.

In this embodiment, User A logs into the client 101 and is identified and authenticated as required using biometrics as described in corresponding U.S. patent application Ser. No. 11/790,843, in step 401 (see FIG. 3). User A may also connect to any additional equipment (i.e., blood pressure monitors etc.) that is required to implement the present invention, in step 402.

In response to User A's selection of a computer-based program, the program 110 will display in step 403, the relevant program, which may include, but is not limited to the following: a web-browser for the internet; a software program (word processing, presentation slides etc.); an EMR; a PACS display program; an on-line education program; an engineering program (CAD, etc.); an architectural program; a calendar (scheduler); a banking program; an e-mail program; etc.

The program 110 will then display for User A, a list of questions in step 404, which relate to at least one of the following: intelligence, personality, emotional state, computer experience, sensory and motor skills, and education and training. The responses by User A will provide the program 110 with information that can be used by the program 110 for analysis of User A's profile. Once the program 110 has analyzed User's A responses in step 405, the program 110 will then come up with a test case scenario in step 406 for User A, which will provide User A with choices—whether automatic or user-driven—which will assist User A in interacting with the computer program.

In this exemplary embodiment, User A's responses were analyzed by the program 110 with a result that shows that User A is highly susceptible to emotional swings and as a result, has fairly high fluctuations in workflow and is easily distracted by external stimuli. Thus, the profile generated by the program 110 in its test scenario, would question User A as to certain preferences User A may have with respect to his use of the computer program. Based on the responses of User A to the test scenario, the program 110 generates a profile of User A in step 407, which User A can apply to the computer program, either automatically, or based on User A's choice. Once the profile is chosen and its application (i.e., automatic or user-driven) is designated, the profile is put into effect with every computer program User A utilizes in step 408. User A has the ability to turn on/off the profile, but use of the profile would assist User A in adapting the computer program to his individual needs.

In this exemplary embodiment, as a result of User A's significant changes in emotional state, the program 110 would determine in step 409 that real-time affective computing measures are critical in identifying when computer and environmental interventions are required to maintain User A's performance. These interventions may include, but are not limited to, simplification of the user interface, reprioritization of the work queue, use of automated protocols, and introduction of calming background music in step 410. Each intervention is tracked by the auditing tool in step 411, and the profile updated in step 412, and stored in step 412, by the program 110.

Due to the relative lack of computer experience and lack of physical impairment with User A, a computer mouse is selected by the program 110 as the input device 104 of choice. As this highly intelligent user becomes more computer literate and willing to expand his computer skills, a multi-programmable mouse may be suggest by the program 110, along with the addition of more sophisticated workstation tools.

In another exemplary embodiment, User B is a moderately intelligent 58 year-old male professional, with limited computer experience, a low keyed and relaxed personality, and limited motor skills due to a prior stroke.

The previous steps in setting up a profile are performed on User B, as were performed on User A, however, the user profile that was generated by the program 110, shows that User B has a more predictable workflow pattern with minimal variation due to his relatively low stress levels and relaxed personality. As a result, User B's profile shows that he tends to be "slow and steady" and methodical in his work and prefers a predictable and reproducible computer program with minimal variability. The program 110 determines that User B is less interested in learning advanced computer functions and instead relies on the most basic and fundamental functionality to complete his task. The program 110 determines from User B's keystrokes, that due to the recent stroke, he experiences residual weakness and limited mobility in his dominant right hand. As a result, the preferred input device for User B would be that of speech commands or a foot pedal for navigation. As with User A, the profile would be put into place by the program 110 so that User B's interaction with the computer program would be as efficient as possible for his needs.

In another exemplary embodiment, user C is a highly intelligent 36 year-old female professional, with perfectionist tendencies, who is overly emotional, with a moderate degree of computer experience, and excellent sensory/motor skills. User C has certain similarities to User A in that she possesses a labile emotional state, and is prone to large fluctuations in stress throughout the course of the day. Due to her perfectionist tendencies, she demands increased accuracy and high levels of performance, which if not met, significantly add to her already high stress levels.

The program 110 would determine that User C's profile would include the integration of advanced computer applications into the computer system/programs, such as automated decision support, as it simultaneously provides the performance requirements which would be advantageous to this user, while maintaining productivity (without undue stress). User C's high intelligence and motivational levels would provide the impetus for her to access continuous educational and training programs offered by the program 110, to advance her computer savvy and overall functionality. These educational and training programs coupled with User C's excellent sensory/motor skills may make her an ideal candidate for an alternative input device like an electronic stylus as her experience and confidence grows.

In another exemplary embodiment, User D is a highly intelligent male, non-professional, an upbeat optimist, with low stress, extensive computer experience, and good motor/sensory skills. User D has a fun loving style and as a result, he tends to be highly energetic, spontaneous, and impulsive. He is highly efficient and productive at work and his combined personality, high intelligence, low stress levels, and extensive computer experience drives him to regularly explore new computer tools and applications.

As a result, the program 110 would determine User D's profile to be highly receptive to on-line and novel educational aides, along with any other recommendations that the program 110 has to offer. The program 110 would present User D with opportunities to frequently upgrade his standardized protocols and templates in an ongoing attempt to improve User D's performance and challenge himself. These upgrades can take several different forms from customized user interfaces, to alternative input devices, to advanced computer tools.

While the number of potential permutations for different profile groups is immense, a representative group of the four different profiles generally illustrate how the present invention can be adapted to different types of end-users.

Applications of the Invention

While the number of possible applications and variations are without limit, a few relevant examples of use are provided below. These are intended to illustrate how each computer system or program may be adapted to the unique profile and preferences of each individual end-user, with different variable weighting applied, depending upon the task being performed.

a) Internet Surfing

In the course of "surfing" the Internet, each individual user has his/her own styles and preferences, which vary according to the factors of intelligence, computer experience, personality, and motor skills all play important roles in determining how user profile is integrated into the idealized user-specific application. However, since the current model is the same for all users, the application is static and not adapted for each user.

However, in the present invention, the computer application is dynamic and the program 110 can configure the computer application in such a way that it fits the user's "profile". Further, the method of the present invention is dynamic and can constantly change based on evolving user-specific variables (e.g., stress, affect), user-specific workflow (data acquired through the electronic auditing tool), and user-specific preferences.

Accordingly, the user may sign onto the computer using biometrics for authentication/identification. As described above, once the user's authentication is complete, the program 110 will request the user answer a number of questions (related to intelligence, etc.), and then offer a test scenario for the user to answer, in order to complete the profile.

In addition, the User-Specific Profile database is automatically queried by the program 110 and the user-specific profile parameters (if already stored) are applied to the computer application being used.

For example, if the program 110 determines that the user is a self-directed user—one that is extremely focused and targeted in their actions—this program 110 will determine that this user prefers an interface that is task-specific, without any superfluous icons or menus. The self-directed approach minimizes the user's computer program interaction, so that all input is self-directed by the user and the computer remains passive, following user-directed commands.

If on the other hand, if the program 110 determines, or the user wishes to have maximal interaction between themselves and the computer program, such as multiple prompts to assist in the search, navigation, and content delivery, then an interactive approach can be provided by the program 110. This interactive approach can include a series of program 110 generated questions and recommendations with which the user interacts, including, but not limited to user interface graphics, computer icons, textual information, tool bars, and the type of input device.

In the interactive approach, the program 110 would offer the user the choice of the relevant input device, and the program 110 would then display a menu of relevant information (as directed by user input if at user direction instead of automatically provided by the program 110), so that the user may select specific controls or make specific choices. After the program 110 receives the user's input regarding controls etc., all subsequent content displayed by the program 110, is directed by the user input commands.

These different approaches to the user interface have major differences on workflow, with the interactive approach creating numerous additional workflow steps not encountered by the self-directed user interface.

After the user "profile" is in place, the user may input data into the web browser to direct an Internet search. As the browser of the computer program identifies content of interest, the self-directed user navigates through the data independently and uses a minimum of tools, which are task-specific and defined within their user-specific profile.

The "interactive" user will respond to a series of computer-generated inquiries and recommendations by the program 110, as to desired content, functionality, and tools utilized—which may include the mode of content delivery for each specific program selected (i.e., audio, video, text). In this approach, the program 110 is repeatedly making suggestions to the end-user as to how to expand their experience. All the while, the electronic auditing tool of the program 110 of the present invention stores the user-specific responses in the database 124, 128 etc., for later updating and refining of the user-specific protocols in order to incorporate them into the workflow profile for future application.

As part of the profile, the program 110 may present educational aides (e.g., short-cuts) and resources to the user, which will continue the interactive operation between program 110 and user.

Once a user-specific profile is established as in the above, including any subsequent updates based on workflow, preferences, and changing profile parameters, the profile is propagated (via the browser) to all Internet sites queried. This export of the profile to other sites creates a mechanism for the content contained within each of the individual Internet sites to be "customized" to the preferences and profile of the individual user. The user-specific profile data may be stored, updated, and accessed within a centralized profile database 128, for example, to correspond to profile changes over time. The user-specific profile database 128, for example, may also be accessed through the end-user's biometrics signature, allowing it to be portable and accessible on demand to the user.

In the era of ubiquitous computing, where computers drive everyday functions, all computer-implemented devices (e.g., washing machine, ATM) can access the user-specific profile and customize the application according to the user-specific profile and preferences.

In addition to the self-directed or interactive user approaches above, the program 110 may also be taking into account any affective measures that the user is undergoing. The affective measures are recorded in real-time (using affective computing measures) by the program 110 and compared against predefined limits. Accordingly, if stress levels are determined by the program 110, based on the user's responses (i.e., blood pressure, facial changes, stress levels in speech, etc.), to reach critical threshold (relative to user's baseline), a "high stress" response is initiated by the program 110.

The "high stress" response by the program 110 includes a number of interventions such as: automated time out, where the program 110 locks out the user from the client 101; a decrease in number of workstation tools available for use; a simplification of the user interface; environmental changes (i.e., heating/cooling, ventilation, background music/white noise, lighting adjustment); and decrease in navigation speed of the input means 104. When stress levels of the user return to the baseline threshold as determined by the program 110, the user is given the option by the program 110 to return to previous settings, or to remain at a "low stress" state of operation.

Further, if the auditing tool of the program 110 of the present invention detects a change in functionality and/or workflow (relative to the user's baseline status), due to stress etc., automated workflow options (i.e., an electronic wizard) are presented to the user by the program 110. The user can elect to "accept or reject" the program's recommendations for automated workflow, which will be received by the program 110.

In addition, upon completion of the user's usage of the computer program, the program 110 will provide the user with optional menus or pop-ups, etc., to provide feedback to the program 110 for workflow database and profiling protocols. Any recommendations by the user for modifications, are incorporated into customized preferences by the program 110. Thus, when the user elects to perform a new/different computer operation, the sequence is repeated by the program 110.

Also in addition, the program 110 may request that the user pick a list of specific computer applications that are frequently used. For example, the user may be provided by the program 110 with a series of questions to determine relative priorities with respect to the computer applications—i.e., ease of use, productivity/workflow, and accuracy/reproducibility. For each of the "frequently used" computer applications to be used, several different variations of each application is presented by the program 110 to the user for feedback. The user may select individual preferences based on the priority order chosen. The program 110 will record these preferences in the user-specific profile database 128 etc., for future use.

b) Presentation Slides

In another exemplary embodiment, such as a software program used to provide slideshow presentations, the user is largely confined by pre-defined tools and functionality, which remain intact in the profile-specific format. However, with the present invention, the presentation of data to the end-user can be individually based on their pre-defined profile and preferences.

For example, as described above, by using the present invention, the user's preferences and profile would determine several operational components such as icons, graphics, tools, color palettes, and sub-menus. Once the auditing tool has captured a user's workflow and correlated that data with their profile, automated workflow templates can be created that provide the ability of the end-user to switch between manual and automated workflow.

These user-specific templates can range from the most simplistic (bare bones) to the most sophisticated, depending on the user's desire. An inexperienced, highly motivated user can progress in computer software program sophistication by taking advantage of the program's 110 inter-activity and educational aides. As previously discussed, the degree of computer activity is tied to the user's profile and desire to navigate in either a "self-directed" or "computer driven" fashion.

In the slideshow program, for example, integration of various functions such as color schemes, animation, and graphics can be directly tied to a number of user-specific variables by the program 110 including (but not limited to) personality, occupation, audience (i.e., reverse profiling), subject matter, and computer experience.

Based on the collective profile database 128 etc., intrinsic to the application being used (i.e., slideshows), the program 110 can query the database 128 etc. so as to make recommendations to the individual end-user on tools and functions that similar end-users (based on profile and preferences) have utilized in the creation of slideshow sets, and incorporate these modifications into the user's automated template (under the direction of the individual end-user). Thus, a mechanism is created for specific computer applications and programs to have their own unique databases of user profiles, workflow, and functionality.

In the exemplary embodiment, the program 110 would begin by requesting that a new user answer a series of questions that will determine that user's specific preferences as it relates to the input device, user interface, tools, data presentation, and educational aides. These user-specific preferences are then correlated by the program 110 with the individual user's profile (if already stored) to arrive at a customized application for that user.

As the individual user continues to use the slideshow program (and responds to program 110 generated queries and educational programs), the templates are updated and refined by the program 110 based on that user's specific workflow. As updates are developed by the program 110, new functionality and tools are presented to the end-user by the program 110, based on the user's pre-existing profile, preferences, and workflow. This data can also be used by the program 110 or by the programmers to improve the product's functionality by identifying inherent product limitations and flaws within different user profile groups. In the end, the slideshow program is transformed from a static, "one size fits all" application to a dynamic, "user-customized" application.

c) On-Line Education

On-line education is highly variable depending upon the specific task and user being evaluated. Two completely different scenarios are presented to describe how the present invention would be used. The first is for the general application of on-line education for school children and the second is the specialized task for continuing medical education (CME) for health care practitioners. Regardless of the occupation and educational application, the general principles hold true regarding how the invention is used.

For school-related on-line education, the user profile is heavily weighted towards the individual user's age, intelligence, sensory/motor skills, and computer experience. These would obviously be far different for a third grader (computer novice) and a college freshman (computer expert). With the advent of video gaming, sensory/motor skills and computer experience can be dramatically altered over a short period of time and this provides a mechanism for learning, which can be directly tied to the individual user's personality, affect, and preferences.

In order to customize on-line learning, several fundamental questions need to be addressed: 1) how do people (individual users) learn best, and 2) how does attention span and memory affect learning strategies?

These are obviously complicated functions that are directly tied to several variables (part of the user profile) including intelligence, personality, and emotional state.

Once these important factors of learning style and knowledge profiles are incorporated into the comprehensive user-specific profile, this data can be standardized and stored by the program 110 so that each application operated by a user will be automatically customized using the user-profile. For example, an elementary student researching the Incas will have their own specific educational profile automatically assigned as he/she travels from one Internet site to another. The same application of the user's educational profile would take place for the college student researching quantum physics. Since emotional state plays a critical role in learning and dynamically changes over time, the stress and affective measures collected will provide continuous feedback for program modification, based on the user's profile and workflow habits already established.

Each individual end-user processes and assimilates information (data) differently, and this can vary depending upon the specific task at hand. For instance, a user may be more adept at math skills as opposed to language or reading skills. The way data is presented to a specific end-user alters depending upon which skill is being utilized—therefore, an optimal method for each end-user is desired.

At the same time, users will differ in the manner in which they prefer data is displayed, with some users learning more effectively with text-based data, others with graphical data, and others with video data.

In the end, the program 110 will provide a profile which establishes a mechanism for determining how each individual end-user best learns and how the computer application can be modified to improve performance for each individual end-user and each specific task or application.

Electronic auditing data from a large population of end-users can in turn be collected and analyzed by the program 110 for identifying the most efficient workflow patterns within different profile groups. These workflow patterns can in turn be presented to individual end-users (within the appropriate profile group) and offered by the program 110 as an educational resource and default template.

In the second scenario, for the specialized application of CME, the same principles can be applied. Since CME is an ongoing requirement for all healthcare professionals, the manner and timing (when and how) it is done varies according to the individual. As a result, the user's preferences can be integrated into CME content delivery by the program 110.

Some users may prefer self-directed CME while others may prefer "automated delivery" by the program 110, where the program 110 directly integrates the CME into the user's workflow (or when requested by the user), by having the search engines integrate the user profile and specific task being performed into real-time education.

In one example, a radiologist interpreting a brain MRI in a patient with neurofibromatosis may be automatically provided by the program 110 with educational content on the topic (neurofibromatosis) from an on-line educational site which has been pre-selected by the radiologist, when the radiologist makes a tentative diagnosis.

Further, another radiologist may instruct the educational profile (program 110) to automatically update him/her with new journal articles on a particular subject matter of interest. Each time a new article is posted on a predefined database, the program 110 will receive that information and e-mail the radiologist with a link to the journal article. The radiologist will have the capability to open, save, and/or delete the article provided to him/her in a datafile by the program 110. The radiologist's response and actions are recorded into the educational profile database by the program 110 in order to update and refine future searches and delivery of educational content by the program 110.

In another example directed to radiologists, two radiologists (A and B) are identified as having high extraversion scores while the other two radiologists (C and D) have low extraversion scores. Generally speaking, the more extraverted radiologists would be analyzed by the program 110 and results would show a preference for "group" education, while the less extraverted radiologists would show a preference for "solo" educational programs.

However, in another example, radiologists A and B (high extraversion scores) have different computer-based proclivities and experience—where Radiologist A has been using computers for over 10 years and is highly "computer literate", and Radiologist B, has minimal computer experience. As a result, Radiologist B is somewhat slow in adapting to new technical developments. Using the electronic auditing tool of the program 110 to provide data insight into each radiologist's workflow, unique differences are identified by the program 110 as to how Radiologists A and B utilize available technology. Radiologist A may take greater advantage of automated hanging protocols (for image presentation), while Radiologist B may instead be performing the same function manually. By identifying limitations in existing workflow, an educational program for Radiologist B can be created by the program 110 to facilitate technology adoption, in keeping with specific personality preferences.

Radiologists C and D, on the other hand, have been identified by the program 110 as having low extraversion scores and would therefore react more favorably to "solo" educational programs. Radiologist C who has a great deal of computer experience and high functionality quotient, prefers to have quarterly educational CD's sent to him/her, on new technology upgrades and "short cuts" introduced. Radiologist D has minimal computer experience and a low functionality quotient. His/her educational programs are also designed by the program 110 to be "solo", but take the form of an electronic wizard that is provided whenever a time-consuming manual task has been performed with an automated alternative. The auditing tool of the program 110 first identifies the inefficient workflow, launches the automated educational program 110 (in the form of the electronic wizard), which in turn provides a self-instructional program 110 that can be engaged or rejected by the end-user. The auditing tool of the program 110 continually monitors workflow and can provide regular feedback to the end-user as to how the educational program has produced objective changes in workflow. This feedback loop can in turn be used by the program 110 to further modify the educational program, based on combined personality and workflow of each individual user.

d) EMR

In a medical application, each individual user's functional requirements for the EMR are dramatically different, depending upon their specific occupation. The requirements for an internal medicine physician are obviously far different from a vascular surgeon, pharmacist, or nurse. This information is easily discernible based on the user's Education and Training categorical profile assembled by the program 110.

Within a given professional occupation, individual users will differ in a number of ways, for example: display presentation, data input, data analysis, educational aides, and reporting. The individual user's profile and preferences will determine how the computer application is customized by the program 110 and this remains consistent regardless of the software program vendor and the computer-related equipment being used.

For example, if a surgeon is reviewing medical imaging data from a patient, his/her user profile may determine numerous individual variables including: image display presentation, processing algorithms, multi-planar reformatting, measurement tools, decision support, and report presentation. The surgeon's profile will maintain consistency with the computer application regardless of whether it is being utilized from his/her office PC, hospital PACS, or enterprise-wide EMR. If the same surgeon was now reviewing laboratory data from the EMR, their user-profile will determine how the data is retrieved, analyzed, and presented for review. For example, one surgeon may prefer data be displayed in a structured format, another using a spreadsheet format, and another using graphical analysis (charts and graphs).

Accordingly, the user of an EMR by the radiologist may be modified by the program 110 to the user-specific depending on how the radiologist prefers to view the data.

e) PACS

In another medical application, such as a radiology practice, a radiologist must perform multiple tasks, either in parallel or series during the course of interpretation of a medical imaging examination. These tasks include the process of exam selection (from the imaging queue), image display, navigation through the multiple image dataset, image review (also referred to as image perception), data assimilation and interpretation, reporting, and communication.

A number of diverse computer-based tools and applications are available to the radiologist to facilitate these individual and collective processes. While many of these applications are automatically integrated into the workflow process by the program 110, others need to be manually launched by the radiologist. Examples of these radiologist-driven applications include advanced image processing (e.g., multi-planar reconstructions (MPR)), decision support (e.g., computer-aided diagnosis (CAD)), quantitative analysis (e.g., volumetric measurements), and links to pertinent clinical and imaging data (e.g., electronic teaching file data).

In addition, an electronic auditing tool of the program 110 as described previously, provides the means to track the steps each individual radiologist goes through in the complex process of image interpretation and reporting, while recording the use of the PACS workstation tool usage and supporting technologies. This provides a "functionality quotient" for each individual radiologist that can be correlated by the program 110 with a number of clinical and demographic details, such as the exam type, anatomic region, clinical indication, medical/surgical history, patient demographics, and correlating imaging data. These details provide valuable data to the program 110 which allows the program 110 to create a profile on how each individual uses the available technology (specific to exam characteristics).

For example, for a given exam type and indication, one radiologist may use a limited number of computer-based tools and applications (i.e., low functionality quotient), while another radiologist would use a large number of tools and applications to interpret the same imaging exam (i.e., high functionality quotient). These functionality quotients can be derived on a quantitative scale of 1-100 by the program 110, to provide a reliable means as to how each individual utilizes the technology and to provide a reliable means for automating many existing manual functions.

The objective data garnered by the electronic auditing tool of the program 110 can in turn be correlated by the program 110 with the subjective data provided through personality profiling. These combined data provides important information as to the "tendencies" for how different types of users adopt and adapt to technology and provides a basis for developing technology that adapts to the needs, idiosyncrasies, and personalities of users.

At the same time, this combined auditing tool/personality profiling information provides valuable insight for the purposes of enhancing end-user education, automating workflow, and re-engineering of existing computer-based software programs.

In another example related to medical professionals, radiologists who have personality factors which are high extraversion and conscientiousness scores are classified as "go getters", working at a fast tempo with high productivity and efficiency, and devising their own proactive self-improvement program. The polar opposite personality style would have low extraversion and conscientious scores. who are classified as "lethargic"—unenthusiastic, passive, and not goal oriented. "Plodders" have a combination of low extraversion and high conscientious scores, and tend to be methodical, slow workers, and highly reliable (in terms of task completion and overall performance).

Using this knowledge, the program 110 may be implemented with three different versions of a single sub-program (of the program 110), designed to accentuate the positives and minimize the negatives of each respective group. While the inherent functionality of each sub-program is largely one and the same, the manner in which each sub-program runs may be far different.

Although various different method steps and sequences have been described with respect to one embodiment, it would be apparent to one of ordinary skill in the art that the various method steps and sequences can be performed in any order, and with any embodiment described. Further, one of ordinary skill in the art would recognize that various steps and sequences may be omitted, or taken together in entirety without departing from the spirit and scope of the invention.

Thus, it should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of adapting computer programs to user profiles, in a computerized application, comprising:

providing a user with a questionnaire to determine at least one of the user's intelligence, personality, emotional state, computer experience, sensory skills, motor skills, education, and training;

determining a type of user profile based on information received from said questionnaire;

creating a test case for the user based upon user responses to said questionnaire;

receiving and storing user unique preferences received from the user in response to said test case, in a database, for future utilization by the user;

compiling a comprehensive user profile based on said user unique preferences, which is assigned specifically to the user;

tracking and storing all computer functions, tools and commands executed by the user, in said database, to create user and task-specific statistical patterns of utilization of said comprehensive user profile;

modifying said computer programs, user preferences, and comprehensive user profiles, based on results of said tracking step;

receiving affective measurements on said user to determine said emotional state of the user;

modifying said user profiles of said computer programs in response to said measurements; and analyzing said information and said responses relative to groups of users to determine similarities in profiles of different groups of users.

2. The method according to claim 1, wherein said modification of said computer programs includes modifying at least one of a user interface, workstation tools, input device and navigation, image presentation, analysis of information presented, and reporting.

3. The method according to claim 1, further comprising:
tracking changes in the user's utilization of the computer programs over time; and
re-modifying the computer programs in order to accommodate said changes.

4. The method according to claim 1, wherein said affective measurements are taken using biometrics input means.

5. The method according to claim 1, further comprising:
implementing templates in the adaptation of the computer programs, based on said profiles of said different groups of users.

6. The method according to claim 5, further comprising:
providing educational materials to said user during utilization of the computer programs.

7. The method according to claim 6, wherein the user's workflow patterns are analyzed before and after use of said educational materials.

8. The method according to claim 5, wherein said templates are automated workflow templates.

9. The method according to claim 1, further comprising:
utilizing biometrics to identify and authenticate said user prior to said user's utilization of the computer programs.

10. The method according to claim 1, further comprising:
performing an analysis of said database to create best practice templates for different user profile groups.

11. The method according to claim 1, wherein changes in the user's workflow patterns predict changes in the user's profile, and the user is notified of said changes.

12. The method according to claim 1, wherein changes in the user's workflow patterns based on said affective measurements, institute a bi-directional feedback loop with the user, until one of said workflow patterns or affective measurements, returns to a predetermined setting.

13. The method according to claim 1, further comprising:
performing a statistical analysis of said database to determine efficient workflow patterns of the user, and providing said workflow patterns to the user for adaptation thereof by the user, during the computerized application.

* * * * *